(12) United States Patent
Wang et al.

(10) Patent No.: US 12,064,264 B2
(45) Date of Patent: Aug. 20, 2024

(54) PACIFIER SENSOR FOR BIOMARKER MONITORING

(71) Applicants: The Regents of the University of California, Oakland, CA (US); University of Alcala, Madrid (ES)

(72) Inventors: Joseph Wang, La Jolla, CA (US); Aida Martin Galan, La Jolla, CA (US); Juliane R. Sempionatto-Moreto, La Jolla, CA (US); Alberto Escarpa, Madrid (ES); Laura Garcia Carmona, Madrid (ES); Maria Cristina Gonzalez, Madrid (ES)

( * ) Notice: Subject to any disclaimer, the term of this patent is extended or adjusted under 35 U.S.C. 154(b) by 0 days.

(21) Appl. No.: 17/246,453

(22) Filed: Apr. 30, 2021

(65) Prior Publication Data
US 2021/0338157 A1   Nov. 4, 2021

Related U.S. Application Data

(60) Provisional application No. 63/018,343, filed on Apr. 30, 2020.

(51) Int. Cl.
| | | |
|---|---|---|
| *A61B 5/1486* | (2006.01) | |
| *A61B 5/00* | (2006.01) | |
| *A61B 5/145* | (2006.01) | |
| *A61B 5/1455* | (2006.01) | |
| *A61J 17/00* | (2006.01) | |

(52) U.S. Cl.
CPC ............ *A61B 5/682* (2013.01); *A61B 5/0002* (2013.01); *A61B 5/14507* (2013.01); *A61B 5/14532* (2013.01); *A61B 5/1455* (2013.01); *A61B 5/1486* (2013.01); *A61J 17/10* (2020.05); *A61J 2200/70* (2013.01)

(58) Field of Classification Search
CPC ... A61B 5/682; A61B 5/0002; A61B 5/14507; A61B 5/14532; A61B 5/1455; A61B 5/1486; A61J 17/10; A61J 2200/70
See application file for complete search history.

(56) References Cited

U.S. PATENT DOCUMENTS

| | | | | |
|---|---|---|---|---|
| 7,228,789 B1 * | 6/2007 | Mondszein | ............ | B65D 85/73 |
| | | | | 220/203.11 |
| 2005/0214532 A1 * | 9/2005 | Kosak | .................. | C12Q 1/6813 |
| | | | | 428/364 |

(Continued)

OTHER PUBLICATIONS

Agrawal, et al., J. Diabetes Metab. 2013, 4, 1000266.

(Continued)

*Primary Examiner* — Puya Agahi
*Assistant Examiner* — Grace L Rozanski
(74) *Attorney, Agent, or Firm* — Perkins Coie LLP

(57) ABSTRACT

Disclosed are sensor devices, systems, and methods for performing electrochemical measurements. The sensor device includes a flexible orthodontic device substantially cylindrical in shape with a hole in an end configured to allow saliva to pass. The device further includes one or more valves to allow the saliva to pass in a forward direction through the flexible orthodontic device and not in a reverse direction, and one or more electrochemical electrodes configured to contact the saliva, wherein the one or more electrodes are configured to determine the presence of one or more chemical biomarkers in the saliva.

21 Claims, 12 Drawing Sheets

(56) References Cited

U.S. PATENT DOCUMENTS

| | | | |
|---|---|---|---|
| 2007/0239068 A1* | 10/2007 | Rasch-Menges | A61B 5/14514 600/576 |
| 2016/0288983 A1* | 10/2016 | Chin | A61J 7/0015 |
| 2019/0099129 A1* | 4/2019 | Kopelman | A61B 5/682 |
| 2020/0060945 A1* | 2/2020 | Evans | A61J 17/02 |
| 2021/0236028 A1* | 8/2021 | McCanless | A61B 5/14503 |
| 2021/0331034 A1* | 10/2021 | Coultes | A61H 23/02 |

OTHER PUBLICATIONS

Aguilar, et al., J. Neonatal diabetes mellitus. Endocr Rev. 2008, 29, 265-91.

Arakawa et al., Mouthguard biosensor with telemetry system for monitoring of saliva glucose: A novel cavitas sensor. Biosens. Bioelectron. 2016, 84, 106- 111.

Bandodkar, et al., J. Non-invasive wearable electrochemical sensors: a review. Trends Biotechnol. 2014, 32, 363-371.

Bruen, et al., Glucose Sensing for Diabetes Monitoring: Recent Developments. Sensors 2017, 17, 1866.

Burrage, et al., "Branched-chain amino acid metabolism: from rare Mendelian diseases to more common disorders", Hum. Mol. Genet. 2014, 23, 1-8.

Chicharro, et al., Saliva Composition and Exercise. Sports. Med. 1998, 26, 17-27.

Fosel, Transient and permanent neonatal diabetes. Eur. J. Pediatr. 1995, 154,944-948.

Grassi, et al., Sensorized pacifier to evaluate non-nutritive sucking in newborns. Med. Eng. Phys. 2016, 38, 398-402.

https://imagine.cc/projects/imagine-express/2018/chupa-chip (Viewed on Dec. 2, 2018). https://patentimages.storage.googleapis.com/15/66/83/64f0b99b73386a/US200 40220498A1.pdf (Visited on Dec. 2, 2018).

https://www.pacif-i.io/ (Viewed on Dec. 2, 2018).

Huang, et al., Particle free optical imaging of flow field by liquid crystal polarization. 2018. Optics Express, 26, 10452-10461.

Kean, et al., Biodegradation, biodistribution and toxicity of chitosan. Adv. Drug Deliv. Rev. 2010, 62, 3-11.

Kim, et al., Wearable non-invasive epidermal glucose sensors: A review. Talanta. 2018, 177, 163-170.

Kim, et al., J. Non-invasive mouthguard biosensor for continuous salivary monitoring of metabolites. Analyst, 2014, 139, 1632-1636.

Kumar, et al., Correlation of salivary glucose, blood glucose and oral candidal carriage in the saliva of type 2 diabetics: A case-control study. Contemp. Clin. Dent. 2014, 5, 312-317.

Lurie, et al., Mechanism of venous valve closure and role of the valve in circulation: a new concept. J Vasc Surg. 2003, 38, 955-961.

Makila, et al., A study of ascorbic acid in human saliva. Oral Biol., 1969, 14, 1285- 1292.

Mannoor, et al., Graphene-based wireless bacteria detection on tooth enamel. Nat. Commun. 2012, 3, 763.

MARTÍN, et al., Epidermal Microfluidic Electrochemical Detection System: Enhanced Sweat Sampling and Metabolite Detection. ACS Sens., 2017, 2, 1860-1868.

Montiel, et al., Delayed Sensor Activation Based on Transient Coatings: Biofouling Protection in Complex Biofluids. JACS, 2018, DOI: 10.1021/jacs.8b08894.

Ngamchuea, et al. Compton, R. G. Analyst, 2018, 143,81-99.

Oncescu, et al., Smartphone based health accessory for colorimetric detection of biomarkers in sweat and saliva. Lab Chip 2013, 13, 3232-3238.

Sashikumar, et al., Salivary glucose levels and oral candidal carriage in type Il diabetics. Oral. Surg. Oral. Med. Oral. Pathol. Oral. Radiol. Endod. 2010, 109, 706-711.

Soukup, et al., Salivary uric acid as a noninvasive biomarker of metabolic syndrome. Diabetol. Metab. Syndr., 2012, 4, 14.

Yang, et al., Wearable and flexible electronics for continuous molecular monitoring. Chem. Soc. Rev., 2019. (DOI: 10.1039/c7cs00730b).

Zhang, et al., Noninvasive glucose monitoring using saliva nano-biosensor. Sensing and Biosensing Research. 2015, 4, 23-29.

\* cited by examiner

PACIFIER SENSOR FOR BIOMARKER MONITORING

CROSS-REFERENCE TO RELATED APPLICATIONS

This patent document claims priority to, and the benefit of, U.S. Provisional Patent Application No. 63/018,343 entitled "PACIFIER SENSOR FOR BIOMARKER MONITORING" filed on Apr. 30, 2020, the entire contents of which are incorporated by reference as part of the disclosure of this patent document.

TECHNICAL FIELD

This patent document relates to sensors including wearable sensor having electrodes.

BACKGROUND

Diverse approaches and devices have been proposed for sensing of biomarkers in saliva. Saliva is suitable for monitoring biomarkers in babies because of its accessibility and availability and the correlation between levels of biomarkers in saliva and corresponding results of common invasive blood tests. The most recent approaches include mouthguards, intraoral dental accessories and sensors included in a lollipop. New methods and devices are needed to better monitor and determine biomarkers in saliva.

SUMMARY

Disclosed are methods and devices for a wearable pacifier-based sensor for non-invasive monitoring of biomarkers present in saliva.

In one aspect, a sensor device is disclosed for performing electrochemical measurements. The sensor device includes a flexible orthodontic device for placement in a patient's mouth, the flexible orthodontic device having a hole in an end configured to allow saliva to pass. The sensor device further includes one or more valves to allow the saliva to pass in a forward direction through the flexible orthodontic device and not in a reverse direction, and one or more electrochemical or optical electrodes configured to contact the saliva, wherein the one or more electrodes are configured to determine the presence of one or more chemical biomarkers in the saliva.

In another aspect a method of performing electrochemical measurements is disclosed. The method includes receiving saliva through a flexible orthodontic device substantially cylindrical in shape with a hole in an end. The method further includes passing the received saliva through one or more valves allowing the saliva to pass in a forward direction and not in a reverse direction, and contacting the saliva by one or more electrochemical or optical electrodes, wherein the one or more electrodes are configured to determine the presence of one or more chemical biomarkers in the saliva.

In yet another aspect, an electrochemical measurement system is disclosed. The system includes an inlet module comprising a flexible orthodontic device configured to pass saliva. The system further includes a valving module allowing the saliva to pass in a forward direction through the valving module and not in a reverse direction. The system includes a contact module including one or more electrochemical or optical electrodes configured to generate signals in response to contact with saliva, and a processing module to process the generated signals to determine the presence of one or more chemical biomarkers in the saliva.

DETAILED DESCRIPTION

Figure 1A:
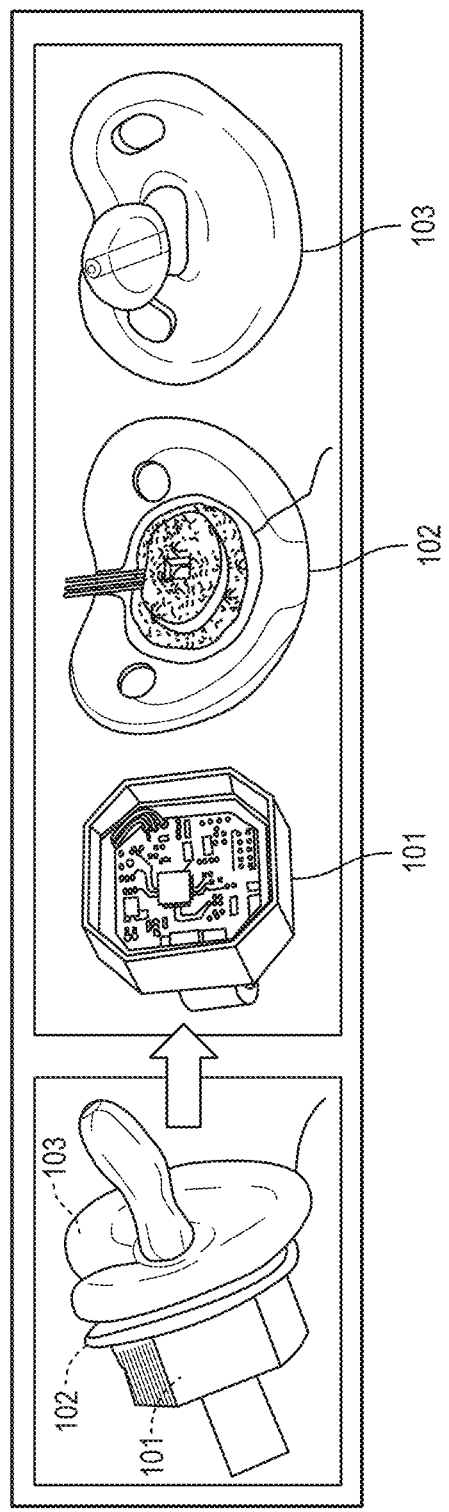
FIG. 1A depicts an example of a pacifier sensor assembly.

Disclosed are methods, devices, and systems for a wearable pacifier-based sensor for non-invasive monitoring of biomarkers present in saliva, in infants, neonates, children, and adults. For example, the biomarkers can include glucose, lactate, uric acid, cortisol, as well as other biomarkers. The pacifier may combine a fluidic design integrated into the pacifier's nipple for sampling saliva directly from the mouth. The pacifier is coupled to a detection chamber and sensor electronics to provide real-time wireless data transmission of biomarker information. The detection chamber combines a disposable electrochemical (or optical, colorimetric) system including one or more biomarker-selective electrodes. In some example embodiments, the disclosed devices and methods may be used to monitor a patient's glucose in saliva. For example, glucose may be monitored in healthy and type I diabetes patients under fasting and meal intake states. Monitoring for other biomarkers and related disorders can be performed as well.

Disclosed herein is a new pacifier-based electrochemical device for (bio)chemical sensing including monitoring of biomarkers related to metabolic diseases. The performance of the new biosensor has been evaluated on-body through glucose determination in saliva from healthy and type I diabetes patients under fasting and meal intake states, demonstrating the applicability for real-time monitoring of diabetes in saliva.

In one aspect, a wearable pacifier-based device is disclosed for non-invasive monitoring of biomarker in saliva such as saliva from infants, children, adults, or various animals. Mouth movement on the pacifier nipple is translated to efficient pumping of saliva to an electrochemical detection chamber. In some example embodiments, the detection chamber contains a glucose oxidase enzyme and a glucose oxidase-modified electrode. The orthodontic device (also referred to as the nipple) includes a combination of valves in the main channel, which causes unidirectional flow from the mouth to an electrochemical detection chamber; along with a second thread, which permits the lateral flow to the outside of the pacifier, respectively. Characterization of the saliva flow conditions in the disclosed device has demonstrated that the biofluid can be collected and eliminated without external pumps and without hindrance to the wearer. Amperometric biosensing of glucose from the rapid saliva collection using glucose oxidase can be done in about 100 seconds (s), or even less. In some example embodiments, the results can be wirelessly monitored during a baby's activity. The electrochemical capabilities were studied in diabetic adult individuals and compared to their blood levels with good correlation. This ability to monitor glucose levels introduces new possibilities for effective diabetes management in infants and paves the way for new metabolic diseases sensing.

Disorders related to the physiological levels of carbohydrates are responsible for several metabolic diseases. In particular, diabetes in newborns and infants is one of these metabolic diseases, affecting to one per 300-500 thousand live births. The majority of these cases present intrauterine growth retardation, failure to thrive, decreased fats, and low or undetectable C-peptide levels. For human babies, strict control of metabolites is needed to avoid damage, especially important in the first days of life because of potentially irreversible damage. Early detection of metabolic diseases requires low-cost and user-friendly platforms for rapid, portable and easy monitoring using non-invasive sampling, which is extremely important in newborn monitoring. In this regard, wearable sensors using various non-invasive approaches may be used for glucose monitoring in different human fluids such as sweat, saliva, urine, and interstitial fluid. Saliva is one of the most suitable biofluids for diabetes monitoring in newborns and babies because: (1) the easy accessibility of sample, (2) the large availability of saliva in babies compared with other biological fluids and (3) the comparable levels of glucose with commonly invasive blood tests.

Challenges in some previous systems include uncomfortable long-term exposure and an electrode surface that includes toxic protective layers to prevent biofouling and maintain electrode stability, such as, poly(o-phenylenediamine), which has carcinogenic or neurotoxic effects. To improve the practical use of glucose sensors, more comfortable devices are needed such as the devices disclosed in this patent document, in which the electrodes are not in contact with the mouth and include non-toxic materials to avoid the leaching of potential harmful components to the digestive system, which may cause serious illnesses.

In one aspect, a wearable saliva biosensing pacifier is disclosed for real-time amperometric monitoring of glucose in newborns and infants. The biosensor uses an enzymatic approach based on glucose oxidase modified prussian blue (PB)-based electrode. The gluco-pacifier shown in FIG. 1A shows a device including a cap at 101 integrated with a wireless amperometric circuit that can include a Bluetooth Low Energy communication system for miniaturization and low-power operation, an electrochemical chamber at 102 to contain saliva for a separated electrochemical detector (avoiding leakage of materials from the electrodic surface), and a non-toxic polymeric nipple at 103 with an inlet for collecting saliva and for saliva sampling comprising a safety valve system, which provides uni-directional saliva flow towards the electrochemical detector. This safety channel includes a rectifying channel with similar functionality to vein valves in humans which use asymmetrical conical constrictions placed in the main saliva collecting tube, providing easy sample collection, measurement and elimination through a cellulose-based thread, improving the comfortability to the wearer.

Figure 1B:
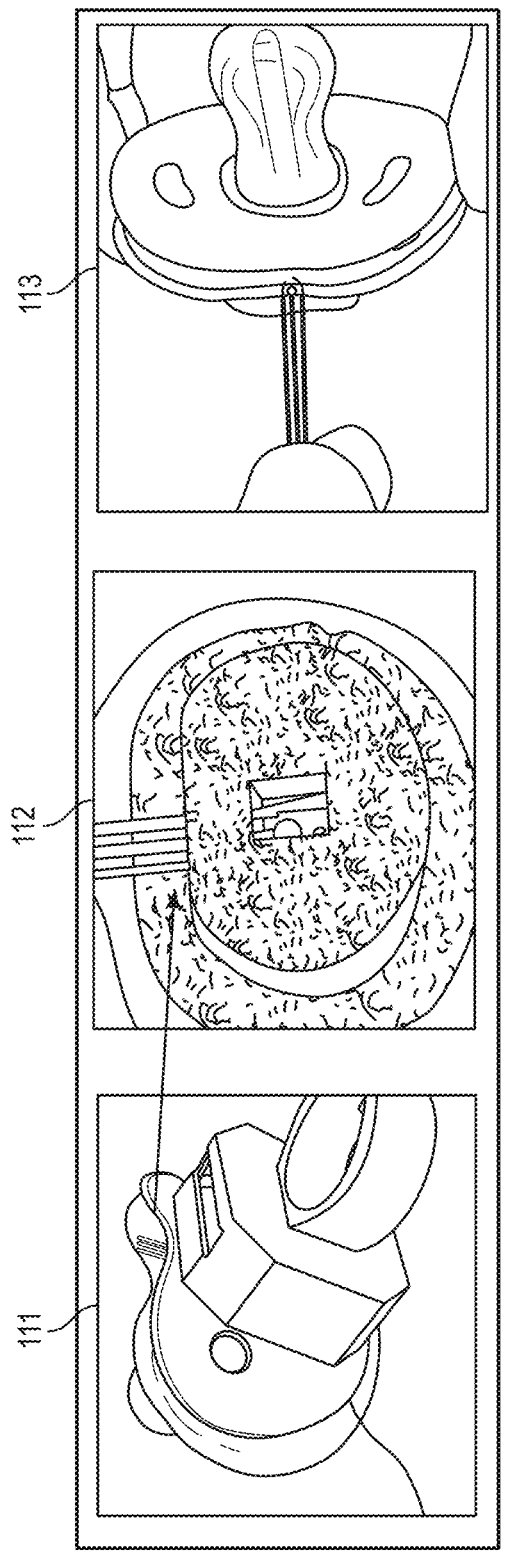
FIG. 1B depicts an example of an electrode placement into the pacifier.

FIG. 1B depicts an example of an electrode placement into the pacifier at 111, the electrochemical chamber at 112, and at 113 a disposable electrode replacement from the pacifier.

Figure 1C:
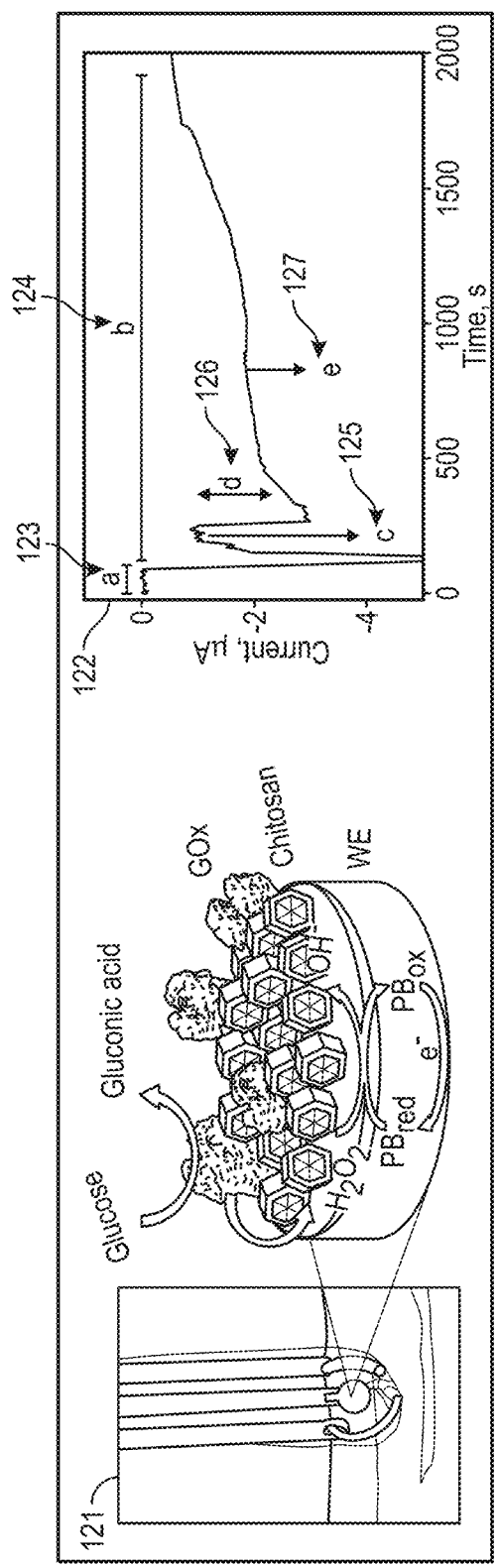
FIG. 1C depicts an example schematic of biosensor electrode operation.

FIG. 1C at 121 depicts an example schematic of a biosensor electrode operation, and a zoomed-in view of the schematic showing the glucose enzymatic biosensing approach on the PB electrode. FIG. 1C at 122 shows example signals corresponding to a dry device at 123, sensor performance with saliva at 124, current before GOx reaction at 125, glucose signal at 126, and current after GOx reaction at 127.

In some example embodiments, the electrodes in the device are fabricated via screen printing process. For example, a semiautomatic MMP-SPM screen printer (for example, Speedline Technologies, Franklin, MA, USA) and stainless-steel stencils with dimensions of 12 in×12 in may be used. A reference electrode and the conductive contacts may be printed on a flexible polyethylene terephthalate (PET) sheet with Ag/AgCl ink (for example, E2414, Gwent Inc., Torfaen, UK). The printout may be cured at 85° C. for 15 min. Then, carbon-prussian blue (PB) ink (for example, C2070424P2, Gwent Inc., Torfaen, UK) may be used to print the working and counter electrodes using the same curing procedure. Finally, an insulating paint may be used to define the electrode area (for example, Aleene's, Inc., Fresno, CA) using the same curing procedure.

The biosensor employed may involve the use of any type of enzyme-based electrode such as the biosensor modification including 0.5 uL layer of chitosan (for example, Sigma-Aldrich, St Louis, MO USA) 0.5% w/v, which may be drop-casted into the working electrode and dried at room temperature. Next, 0.5 μL of with glucose oxidase (GOx) from *Aspergillus niger* type X-S (EC 1.1.3.4) (for example, Sigma-Aldrich, St Louis, MO, USA) in a 34 mg/mL concentration prepared in 0.1 M phosphate buffer, pH 7.4 (for example, Panreac, Spain) may be drop casted into the working electrode and dried overnight at 4° C.

The pacifier biosensor may be fabricated using pacifiers such as: a nipple (for example, Orthodontic pacifier 0-3 month, silicone, NUK, USA) and a core containing a chamber (for example, Juicy Orthodontic Pacifier, 0-6 months, NUK, USA). The nipples used for saliva flow studies may be silicone nipples (for example, Gerber First essentials, USA). An inlet hole may be created in the nipple using a 4 mm diameter biopsy punch (Biopunch, Redding, US).

The cap of the pacifier containing the electrochemical cell may be customized using a 3D printer. The acrylonitrile butadiene styrene (ABS)-based 3d printed piece (2.4×1.8× 0.7 $cm^3$) may include a chamber (such as but not limited to 4×4×4 $mm^3$) for performing the electrochemical measurements and a 0.5×0.5 $mm^2$ hole at the right bottom corner, which connected the measurement chamber with the outside of the pacifier by a hydrophilic cellulose-based thread shown in FIG. 1A. Additionally, an external 3D case can be further incorporated for the fully-integration of potentiostat and the battery for future applicability.

The saliva sampling may be done by using a customized uni-directional rectifying channel based on a PVC tube (or other material) including plastic valves along a length. For example, 3.5 cm length and 0.15 cm diameter PVC tube including plastic valves with 6 mm length may be created by cutting pipet tips with the proper shape and size. A hole may be cut on the tip of the nipple using a biopsy punch (for example, Biopunch, Redding, US), and by pressure all the polymeric components were sealed, avoiding possible swallow from the user. This tube ends in the electrochemical chamber, allowing complete soaking of the electrode surface. Finally, a 7 cm hydrophilic cellulose-based thread together with a 1 cm diameter pipette filter (for example, protection filter 10 mL, Eppendorf, Hamburg, Germany) may be placed at the back of the chamber fixed with adhesive blue tack (for example, Bostik, Unipessoal, Portugal) to the pacifier.

Electrochemical measurements may be carried out using a portable multi potentiostat µSTAT 8000P (Dropsens, Oviedo, Spain). Electrochemical analysis, to detect enzymatic product ($H_2O_2$), were performed by amperometry applying −0.2 V vs. Ag/AgCl.

All solutions for the in vitro measurements may be prepared in artificial saliva. The artificial saliva may be prepared by dissolving 5 mM of NaCl (for example, Panreac, Spain), 15 mM of KCl (for example, Sharlab, Spain), 1 mM of citric acid (for example, Fluka, Switzerland), 1 mM of $CaCl_2$, 1.1 mM of KSCN (for example, Merk, Germany), and 4 mM of $NH_4Cl$ (for example, Sigma-Aldrich, St Louis, MO, USA) in distilled water.

The pH of artificial saliva was adjusted to 6.7, which is an average pH of healthy human saliva. D-glucose, uric acid (for example, Sigma-Aldrich, St Louis, MO, USA), ascorbic acid, citric acid (for example, Fluka, Switzerland) were used without further purification and prepared in artificial saliva.

Flow in-vitro studies were performed by pressing the pacifier nipple with the fingers, simulating the mouth suction movement during the pacifier use. Additionally, a blue candy and gel food color (Dr. Oetker), were used as a blue ink to dye real and artificial saliva, respectively, in order to facilitate the saliva flow visualization.

The on-body experiments were performed using saliva from one healthy and two type I diabetic volunteers.

During on-body studies, the volunteers were asked to follow a protocol adapted from an already published procedure. The protocol consisted in: (1) Brush the teeth using toothpaste and carefully rinse the mouth with plentiful water, avoiding toothpaste residue. This step is done before the saliva testing, to avoid possible glucose contamination. (2) Minimize swallowing and hold saliva in mouth (typically <1 min). (3) Collect raw saliva in a clean 2 mL eppendorf (only in case of diabetic patients). After that, saliva and blood glucose levels were measured before and after food intake in diabetic patients. For on-body measurements, a commercial glucometer Glucocard G Meter was used to assess glucose blood concentration (Arkray, MN, USA).

A time-correlation for the highest values of glucose in saliva and blood was established and it was noticed that salivary glucose value reaches its peak value 15-40 min after food intake while the blood glucose increases to its highest value around 30-60 min in healthy subjects and 1-2 h after in diabetic patients after food intake. Thus, in all subjects, saliva and blood glucose was measured 30 and 60 mins after intake in saliva and blood, respectively, for a better correlation of the data.

Initially, a baseline was measured without any saliva, then, the pacifier was used taking 200 s for the saliva to reach the electrode. After GOx reaction takes place, a stable signal is obtained within 100 s. Afterwards, real time glucose signal is continuously monitored as long as the saliva remained inside the reservoir. When the outlet completely removes the moisture, the signal is back to the baseline. Electrodes were disposed of the sensor between experiments. Nipples were sterilized with ethanol and/or disposed after use between experiments.

A wearable biosensor based on a pacifier has been designed to fit the challenge of collecting and measuring glucose in saliva in newborns and infants. As noted above, FIG. 1A shows an example of a device including an integrated portable potentiostat for the measurements, an electrode chamber, and a nipple for the saliva collection. A miniaturized potentiostat with a Bluetooth Low Energy radio can enable wireless connection from the glucose sensor to a host device, such as a smartwatch, smartphone or laptop. A portable potentiostat USB-connected to a laptop may be used. Measurements were carried out using the disclosed screen-printed biosensor based on a prussian blue electrode inserted into the slot that ends in a 4×4 $mm^2$ chamber where saliva accumulated to carry out the saliva measurement. See, for example, FIG. 1B at 111 and 112. The disposable nature of the fabricated electrodes enables easy replacement, so the measurement can be performed by non-qualified personnel. See, for example, FIG. 1B at 113. The electrode was fabricated using large-scale and low-cost screen-printing technology on a PET layer including the three electrodes system containing working and counter electrodes based on PB and a reference electrode of Ag/AgCl. Glucose detection was obtained by the selectivity provided by GOx. To this aim, the enzyme is immobilized on the working electrode surface using chitosan, a non-toxic polysaccharide to immobilize the enzyme on the electrode surface. Thus, glucose is oxidized by GOx allowing $O_2$ reduction to $H_2O_2$. Subsequently, $H_2O_2$ is reduced and PB oxidized. The amperometric reduction at −0.2 V closes the redox cycle allowing the glucose monitoring. See, for example, FIG. 1C at 121. FIG. 1C at 122 shows an example monitoring of the pacifier signal. Initially, the device is dry, and the observed current is zero shown at 123. This signal increases when saliva reaches the electrochemical chamber due to capacitive current at 124. Next, it leads to a stable signal. Stability of this signal may be affected by the amount and viscosity of saliva and by the diffusion of the glucose and the enzymatic product to the biorecognition layer and to the electrode surface, respectively at 125. Then, when the enzymatic reaction has been completed, the glucose signal is obtained at 126 and it is proportional to the difference of the current before GOx reaction at 125 and after 126 the enzymatic reaction. Finally, the signal decreases slowly return to the baseline when the saliva is removed from the chamber by the outlet after GOx reaction at 127.

Figure 5:
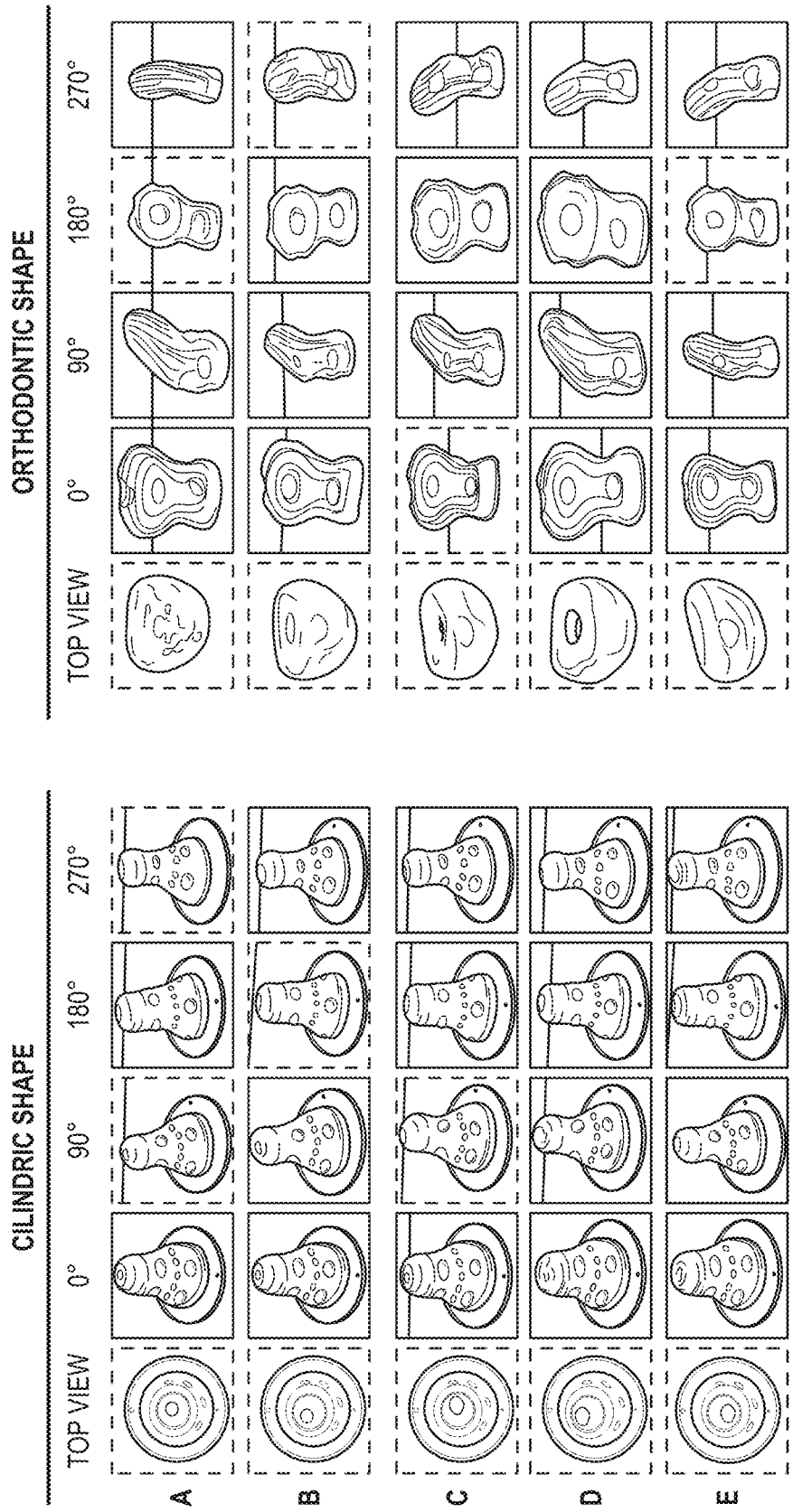
FIG. 5 depicts examples of different nipples (cylindric and orthodontic) and modalities (sitting, lying on the right and left sides, and facing up and down).

Considering the final application of the device and, to find the best location for the inlet, different nipples and body position were studied using an edible blue candy to stain saliva. Cylindric and orthodontic nipples were drilled with 4 mm holes along their whole surface and filled with absorbent white paper. Upon eating the blue-candy, the saliva's volunteer stained blue and the pacifier was used for 30 s. After use, the pacifier was examined to determine, according to the level of dye on the absorbent paper, the different flows of saliva on the nipple. Different nipples (cylindric and orthodontic) and modalities (sitting, lying on the right and left sides, and facing up and down) were explored, being the orthodontic format with the inlet on the tip of the nipple the best location (see FIG. 5).

In some example embodiments, an inlet to collect saliva includes a 3.4 cm long semi-flexible tube from the optimized inlet to the electrochemical chamber. This first channel goes through the nipple, connecting the inlet (facing the mouth) with the electrochemical chamber where the outlet of the tube flows saliva into the chamber (see, FIG. 2A). To ensure the safety of the pacifier biosensor, this first channel has been designed to ensure only forward direction in the saliva flow using a rectifier valve system.

The working principle of these valves is similar to vein valves in humans in the body or other microfluidic triangle-based rectifying channels. Using asymmetrical conical constrictions placed in the middle of the tube, the saliva keeps moving only in one direction, permitting negligible hazard to the user. FIG. 2B at 210 shows the disposition of the valves inside the tube connecting one with the other leading the flow to the chamber. The valves are plastic cone pieces placed one after the other with the thinner side of the valve inside the wide side. Thus, these constrictions enable unidirectional flow, filling progressively the valves and decreasing the death volume of saliva from the nipple to the electrochemical chamber. When the baby is using the pacifier, saliva flows from its mouth through the tube reaching the wide side of the valve, once this first valve is filled, it starts to fill the following one. The resistance of the filled cone valves blocks the saliva for reversing the direction, because the flow in the reverse direction faces more resistance than the forward flow. Therefore, positive resistance, due to the shape and other capillarity effects, when the suction is stopped, the flow in the backward direction is restricted and the saliva does not revert to the mouth. This rectifying channel was shown to be efficient using artificial saliva stained with blue dye. Additionally, the movement of the baby using the pacifier was imitated by applying a perpendicular force in the inlet of the tube with the fingers, inside a small pool containing artificial saliva stained with blue ink, demonstrating the concept. FIG. 2B at 220 shows the efficient sampling using artificial saliva dyed with blue ink, before and after the demonstration experiment.

Figure 2A:
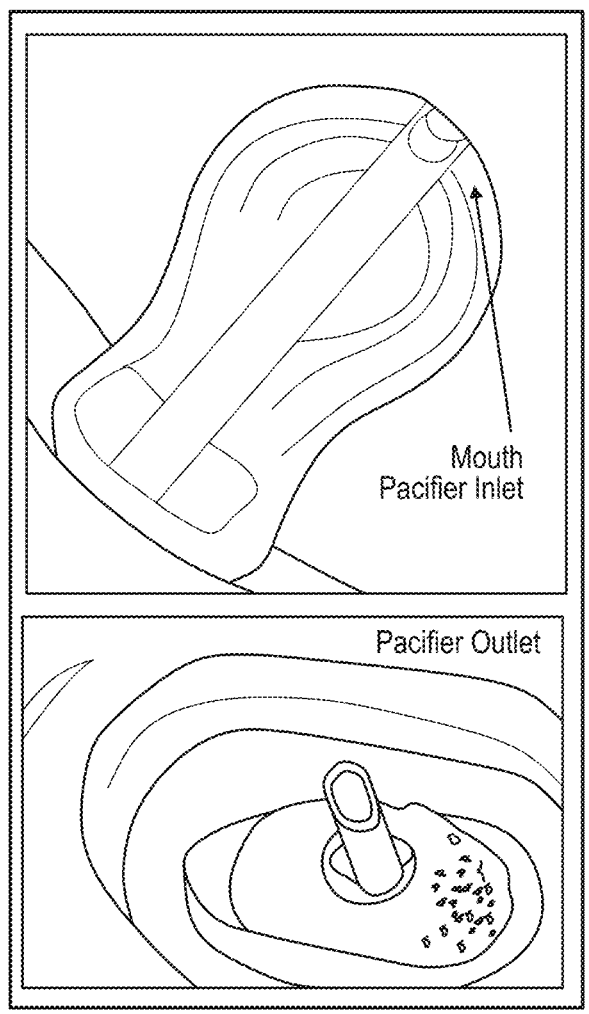
FIG. 2A depicts an example image of the pacifier including an inlet connecting a flow of saliva from the mouth to the outlet facing an electrode chamber.
Figure 2B:
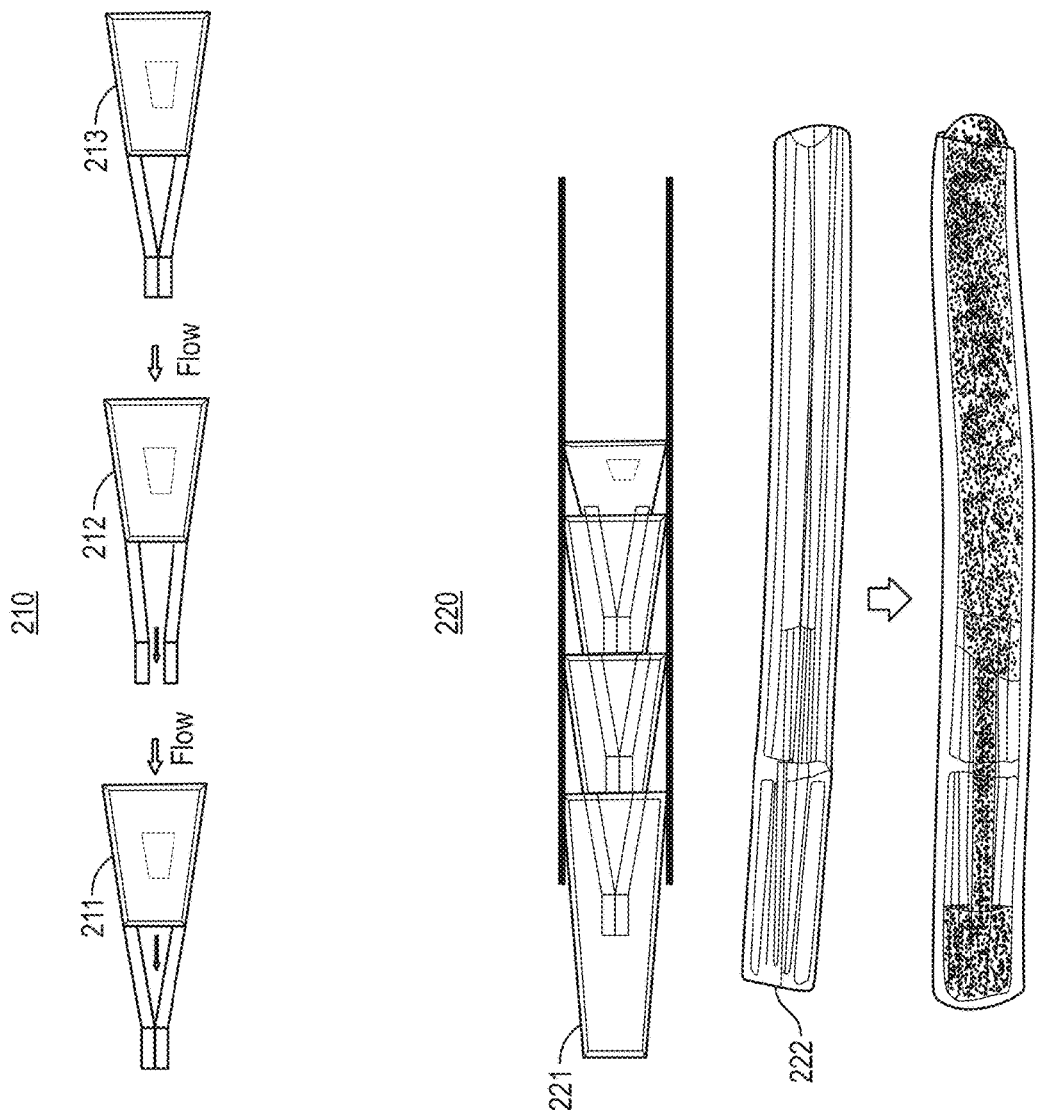
FIG. 2B depicts an example of valves inside a tube leading a flow to a chamber.
Figure 2C:
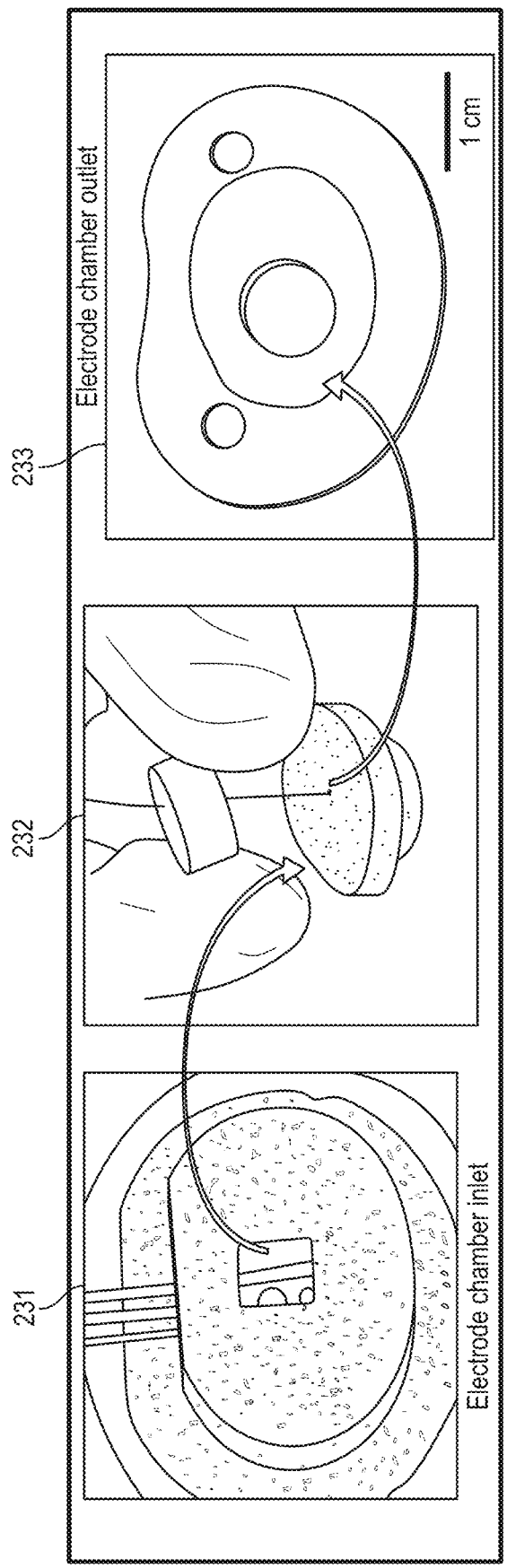
FIG. 2C depicts an example of flow direction from the electrode chamber to the environment.

Once the saliva reaches the sensing chamber, the electrochemical measurement starts once the electrode is facing the outlet of the tube (FIG. 2C at 231). To allow a continuous and completely unidirectional flow a second safety accessory was included to connect the electrochemical chamber to the outside. The fully saliva replenishment in the electrochemical chamber is necessary to avoid carryover during the measurements, allowing successful performance of a new measurement, replacing the saliva already used and avoiding possible overflow of saliva to the electrical contacts or back-flowing to the mouth. To this aim, a small hole (0.5×0.5 mm$^2$) was placed at the right bottom corner containing a hydrophilic thread, connecting the inside part of the cell with the outside of the pacifier. The tread gets soaked inside the electrochemical chamber and the end of the outlet exposed to the air is constantly dried by evaporation, allowing a continuous flow. Additionally, in the same path as the thread, a hydrophilic filter was placed to reduce the drying time (FIG. 2C at 232 and 233). Filter paper can be a good option to be used as an outlets because it provides a fast drying time (800 s) compared to other hydrophilic outlets.

FIGS. 2A-2C depict a characterization of the continuous saliva flow in the pacifier. FIG. 2A depicts a picture of the pacifier including the inlet connecting the flow from the mouth for saliva collection to the outlet facing electrode chamber.

FIG. 2B depicts an example rectifier channel inside the pacifier including a scheme of valves and disposition inside the tube at 210. The valve working principle is as follows: At 211, the valve is closed before the arrival of saliva flow. At 212, the valve is opened. At 213, the valve is closed after saliva flow. FIG. 2B at 220 shows example images showing the tube and integrated valves before and after a use demonstration with artificial stain artificial saliva. Shown at 221 is a schematic of the disposition of the valves inside the tube. Shown at 222 are images of the tube with dyed artificial saliva going through the valves.

FIG. 2C depicts an example of flow direction from the electrode chamber to the environment. At 232 is a front view of the electrochemical cell with an opening at the bottom right corner showing the tip of the thread in contact with the electrode chamber. At 232 is an image of the back part of the chamber including the thread and the filter to soak saliva. At 233 is an image of the back part of the pacifier with the chamber and the outlet already integrated into the pacifier.

Figure 3A:
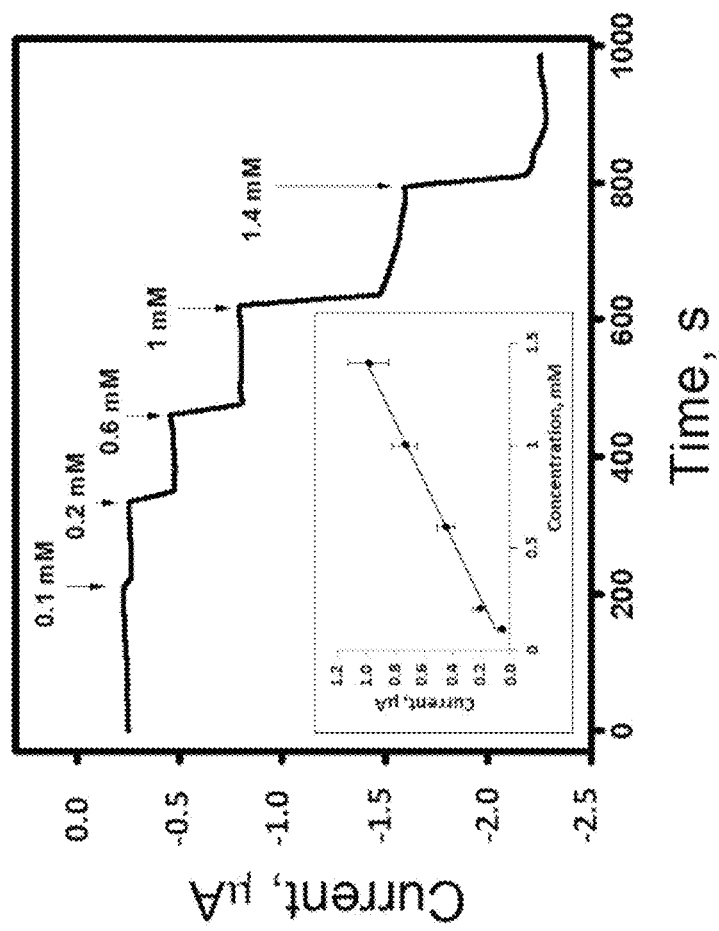
FIG. 3A depicts example amperograms obtained for increasing glucose concentration.

The device can actively and continuously collect and evacuates saliva. Optimization of the glucose detection is needed for the efficient applicability of the sensor. Integrating a disposable printed PB electrode modified by chitosan and GOx, glucose in vitro analysis using amperometry at −0.2 V in artificial saliva was performed. As shown in FIG. 3A, a calibration curve for glucose was carried out in the linear range between 0.1-1.4 mM, which is consistent with glucose concentration ranges in diabetic saliva. In this sense, excellent linearity (R2=0.994), with intercept of 0.04±0.03 nA, and good sensitivity (0.69±0.04 nA mM−1) were achieved. The limits of detection (LOD) and quantification (LOQ) obtained were 0.04 mM and 0.1 mM, respectively, which were enough to quantify the regular levels of glucose in diabetic patients, even before eating. The LOD has been calculated according to the 3 sb/m criteria, where m is the slope of the linear portion in the calibration graph, and sb was estimated as the standard deviation (n=10) of the amperometric signals measured for glucose at the lowest concentration level of the calibration graph.

Excellent inter-sensor reproducibility was also obtained for 0.6 mM glucose, which is a regular glucose concentration in diabetic patients with RSDs ≤10% (n=9). These results show the suitability of the sensor in real applications involving a replacement of the disposable sensor between measurements (before and after food intake).

Uric acid (UA) and ascorbic acid (AA) were also checked as potential saliva interfering compounds for the selective determination of glucose at −0.2 V. In this sense, it can be observed that 0.6 mM glucose produces the expected response whereas uric acid and ascorbic acid did not show any response at the basal concentration of these molecules in saliva (200 μM and 20 μM, respectively). Additionally, it is worth to highlight that the glucose response is not lost after UA and AA measurement, which indicates the low fouling of these molecules on the electrode surface (FIG. 3B).

Figure 3B:
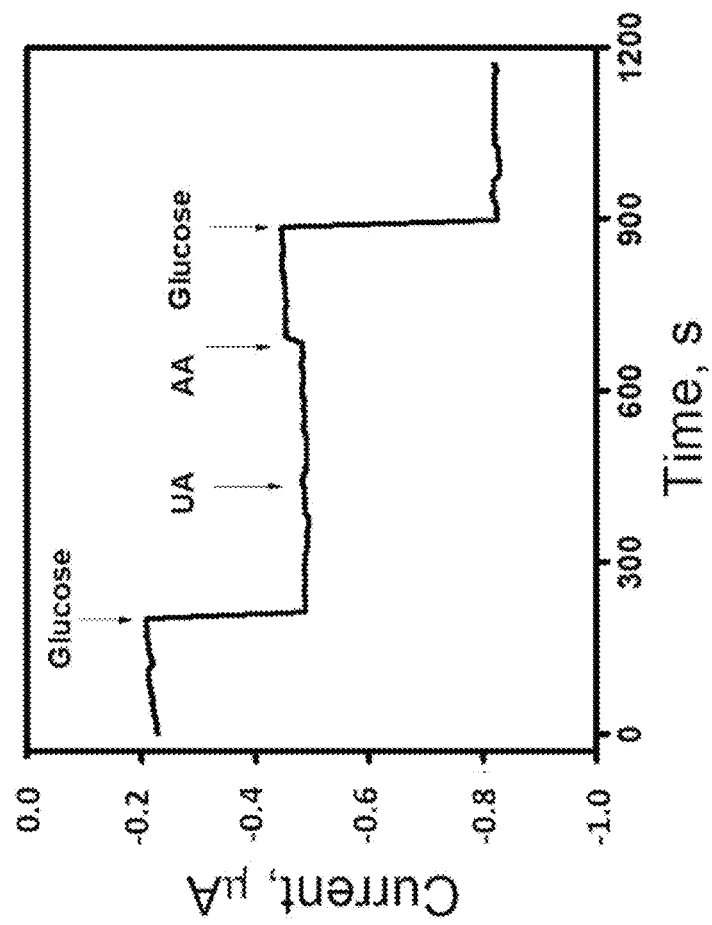
FIG. 3B depicts an example of a selectivity test.

FIGS. 3A and 3B depict examples of the electrochemical performance in artificial saliva. FIG. 3A depicts amperograms obtained for increasing glucose concentration (linear range 0.1-1.4 mM). The resulting calibration curve is shown in the inset. FIG. 3B depicts an example of a selectivity test: response of 0.6 mM glucose in the presence of common electroactive physiological interferents in saliva (200 μM UA and 20 μM AA).

Figure 6:
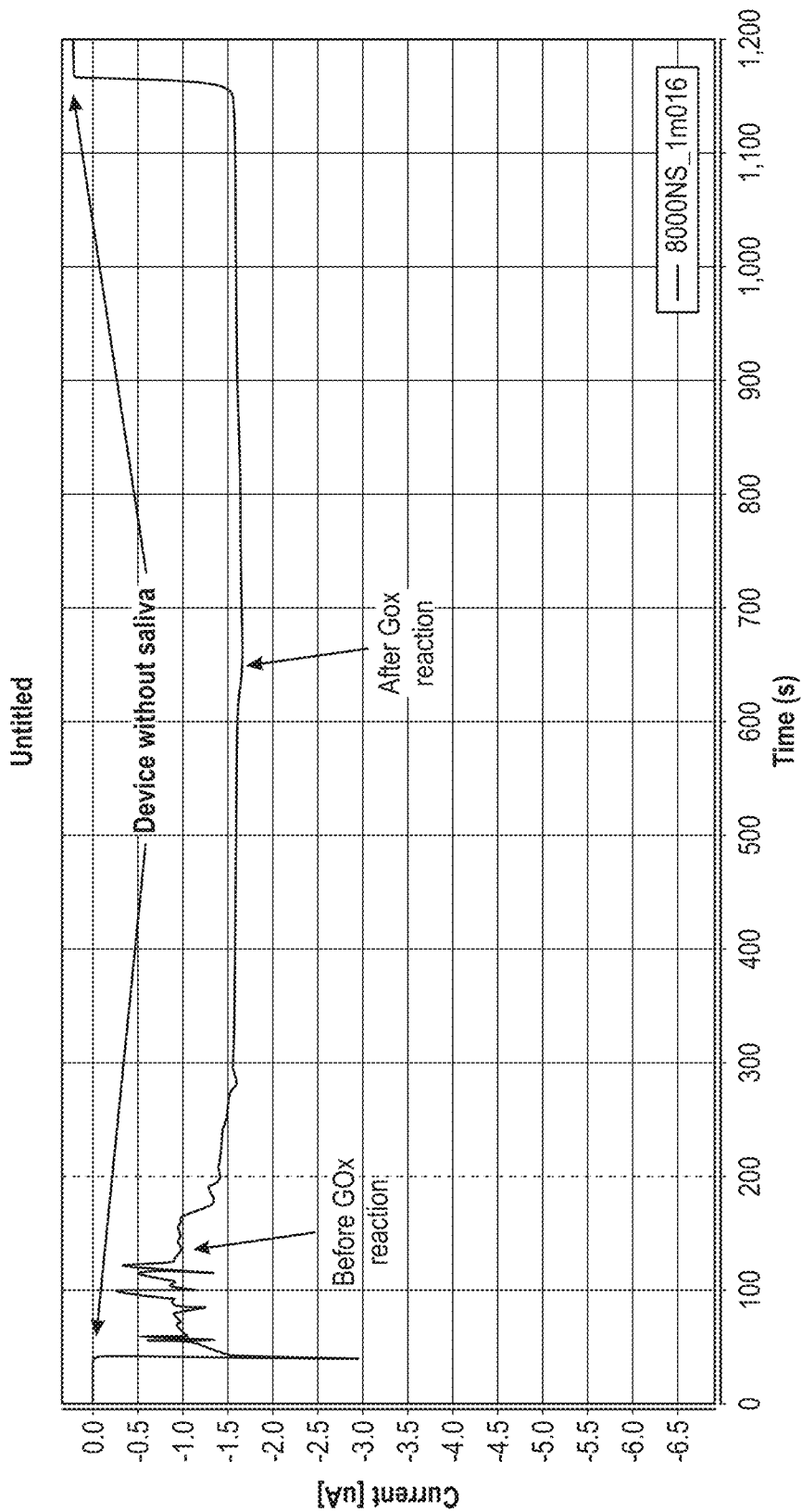
FIG. 6 shows an example of an amperometric signal as a function of time from the pacifier.

A continuous on-body monitoring of glucose in saliva of people was performed. FIG. 6 shows an example of an amperometric signal as a function of time from the pacifier used by a healthy subject after meal. After 200 s of use, the saliva reaches the electrode which provokes an increment in the amperometric signal. This signal is stable after a few seconds and increases (negatively) 100 s later once the reaction with the GOx takes place, due to the presence of glucose in the saliva. The sensor can be used to differentiate healthy and diabetic persons in a fasting state because there is no signal for healthy people in fasting state. However, the concept of the sensor on a pacifier has been proved to monitoring differences between before and after meal glucose concentration in diabetic patients, which would have further implication in newborns and infants. In this sense, the glucose concentration in saliva has been measured using the biosensor in real saliva from two different patients diagnosed with type I diabetes before and after they had a meal. The glucose concentration in saliva before and after meal was correlated with glucose concentration in blood, measured with regular glucometer-fingertip blood, which is a very well-stabilized method for diabetes monitoring.

Figure 4:
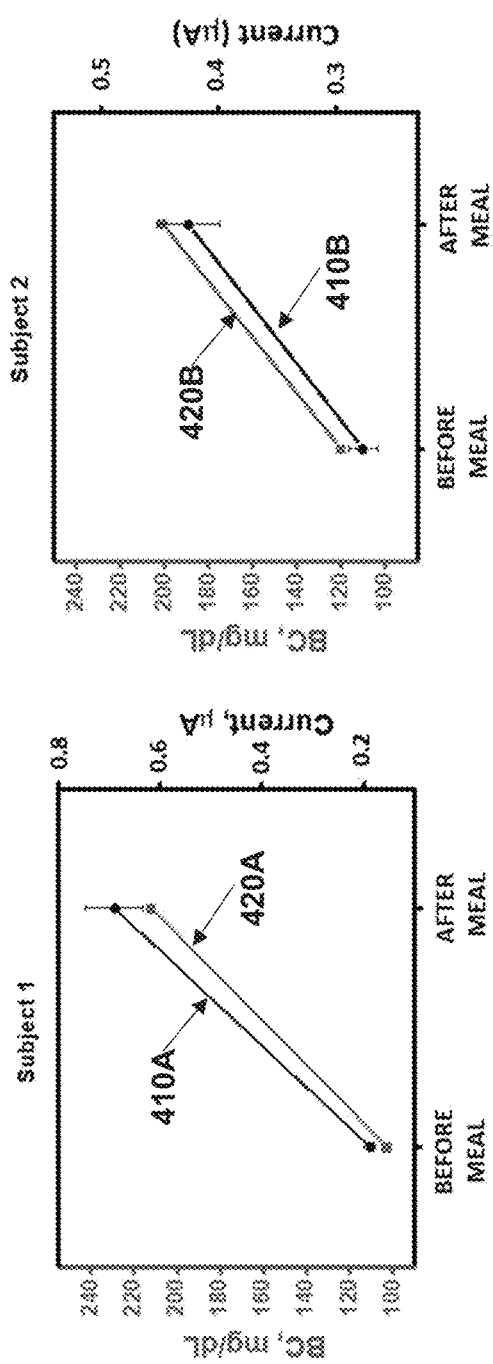
FIG. 4 shows an example of the correlation achieved between saliva and blood levels of glucose before and after meal.

FIG. 4 shows an example of the correlation achieved between saliva and blood levels of glucose before and after meal in the studied individuals, with a good reproducibility and % RSDs of 8 and 9% in the two sample subjects analyzed, respectively. FIG. 4 depicts examples of on body monitoring of glucose levels in type I diabetes subjects. Correlation between current obtained in saliva using the pacifier sensor (410A and 410B) and glucose concentration in blood (420A and 420B) for two subjects Subject 1 (410A and 420A), left plot and Subject 2 (410B and 420B), right plot, before and after meal.

Thus, these data demonstrate the suitability of the disclosed sensor to monitor changes in glucose concentration using saliva from a non-invasive sample. The results obtained including selectivity, sensitivity, and reproducibility between different sensors establish the basis for the clinical applicability of the pacifier in a diabetes monitoring of newborns. The disclosed device provides a new alternative to the current issues related to sample collection involving invasive samples of blood. The disclosed new chemical sensors using the disclosed non-invasive sampling technique is important to human patients, especially newborns. The device may also be used on animals. Additionally, the capability of the sensor to be fully integrated with wireless transduction makes it even more convenient for saliva monitoring in a pacifier, considering also the good results obtained using the active saliva monitoring.

Figure 7:
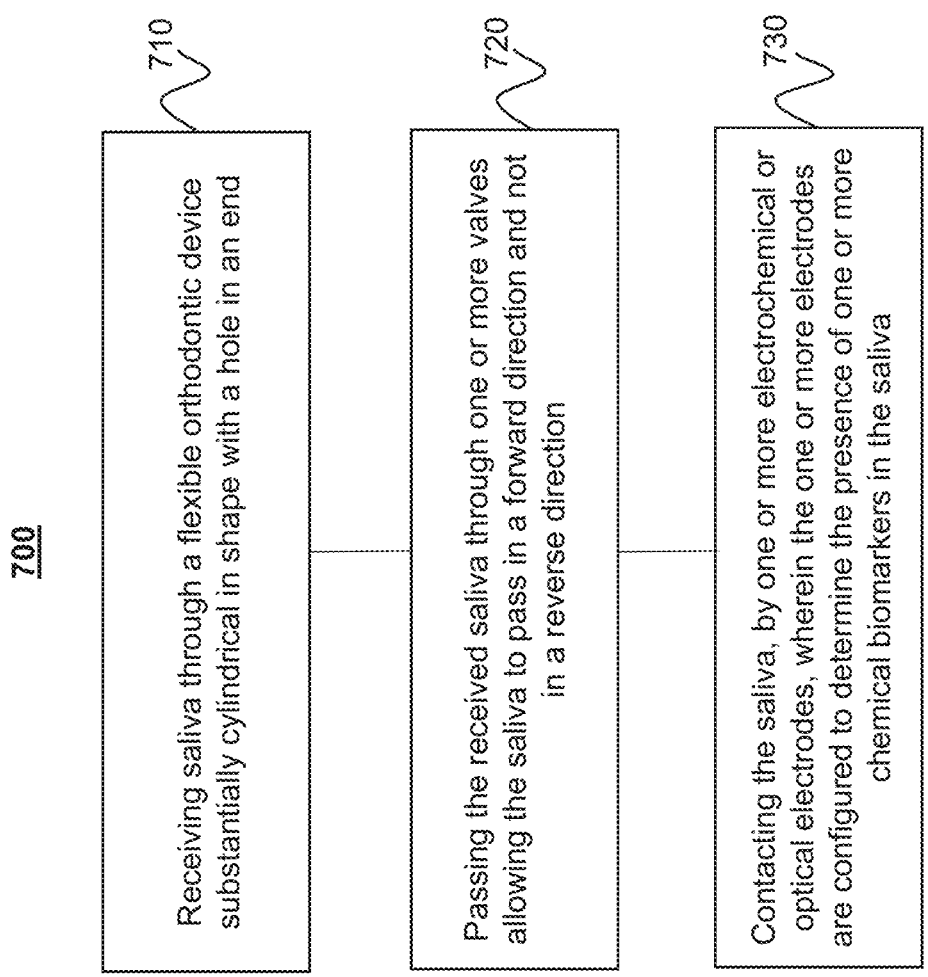
FIG. 7 depicts an example of a process.

FIG. 7 depicts an example 700 of a process. At 710, the process includes receiving saliva through a flexible orthodontic device substantially cylindrical in shape with a hole in an end. At 720, the process includes passing the received saliva through one or more valves allowing the saliva to pass in a forward direction and not in a reverse direction. At 730, the process includes contacting the saliva, by one or more electrochemical or optical electrodes, wherein the one or more electrodes are configured to determine the presence of one or more chemical biomarkers in the saliva.

In summary, disclosed is a pacifier-based electrochemical sensing system for monitoring of glucose integrating sampling and measurement in the same device/platform. The combination of a pump-free system along with the safety concern of providing a unidirectional flow to an external collection outlet facilitates a baby-friendly system. This device is capable of integrating saliva sampling with electrochemical sensing, along with capabilities such as miniaturized wireless electronics on a single pacifier platform. Such integration simplifies infants' diabetes monitoring in a real-time and selective manner. The attractive performance can rapidly alert the wearers and parents about abnormal glucose patterns being possible to be implemented for adults in another accessory. This device could be readily reconfigured and expanded for analyses of a wide range of salivary biomarkers in newborn diseases or monitoring in connection to different printable transducer inks, electrode materials and bioreceptors. Hence, different biorecoginition processes can be used to recognize the target biomarker in the complex sample. Besides fixed potential amperometric, the device can use a wide range of electrochemical techniques, such as (but not limited to) square-wave voltammetry.

In one aspect, a sensor device capable of performing electrochemical measurements is disclosed. The sensor device includes a flexible orthodontic device for placement in a patient's mouth, the flexible orthodontic device having a hole in an end configured to allow saliva to pass. The sensor device further includes one or more valves to allow the saliva to pass in a forward direction through the flexible orthodontic device and not in a reverse direction. The sensor device includes one or more electrochemical or optical electrodes configured to contact the saliva, wherein the one or more electrodes are configured to determine the presence of one or more chemical biomarkers in the saliva.

The sensor device can include the following features in various combinations. The sensor device can include one or more electronic circuits to process signals from the one or more electrodes and/or a wireless transmitter to transmit information from the processed signals to a receiving device. The flexible orthodontic device can be part of a pacifier or a nipple. The one or more electrodes can generate a signal representative of an amount of glucose in the saliva. The one or more electrochemical or optical electrodes can include at least one enzyme-based electrode selected to determine the presence of a selected biomarker of one or more chemical biomarkers in the saliva. The enzyme can be a glucose oxidase. The one or more valves include a combination of valves can be in a main channel causing unidirectional flow of the saliva to an electrochemical detection chamber. A cellulose-based thread can be included that causes a lateral flow of the saliva from the electrochemical detection chamber to an outside of the sensor device. The sensor device can be configured to collect and dispose of the saliva without external pumps. The one or more electrochemical or optical electrodes are not in contact with the patient's mouth. The one or more electrodes are non-toxic. The sensor device can include an electrochemical chamber to contain the saliva. The flexible orthodontic device can include a non-toxic polymeric nipple with an inlet for collecting saliva and a safety valve system causing unidirectional saliva flow towards the one or more electrochemical or optical electrodes. The safety valve system can include a rectifying channel with asymmetrical conical constrictions. The sensor device can include a cap integrated with a wireless amperometric circuit, an electrochemical chamber to contain the saliva for a separated electrochemical detector, and/or a safety valve system causing unidirectional saliva flow towards the electrochemical detector.

In another aspect a method of performing electrochemical measurements is disclosed. The method includes receiving saliva through a flexible orthodontic device comprising a nipple or pacifier with a hole in an end, passing the received saliva through one or more valves allowing the saliva to pass in a forward direction and not in a reverse direction. The method includes contacting the saliva, by one or more electrochemical or optical electrodes, wherein the one or more electrodes are configured to determine the presence of one or more chemical biomarkers in the saliva.

The method can include the following features in various combinations. The method can include processing, by one or more electronic circuits, signals from the one or more electrodes, and/or transmitting, by a wireless transmitter, information from the processed signals to a receiving device. The one or more electrodes can generate a signal representative of an amount of glucose in the saliva. The one or more electrochemical or optical electrodes can include at least one enzyme-based electrode selected to determine the presence of a selected biomarker in the saliva.

In another aspect an electrochemical measurement system is disclosed. The system can include an inlet module comprising a flexible orthodontic device configured to pass saliva, a valving module allowing the saliva to pass in a forward direction through the valving module and not in a reverse direction, a contact module including one or more electrochemical or optical electrodes configured to generate signals in response to contact with saliva, and/or a processing module to process the generated signals to determine the presence of one or more chemical biomarkers in the saliva. The one or more electrochemical or optical electrodes can include at least one enzyme-based electrode selected to determine the presence of a selected biomarker in the saliva.

The disclosed device/platform performs minimally invasive clinical saliva sampling and detection; the device/platform supports user-friendly and fast diagnostics into an electrochemical wearable that can be used by a group of patients with rare diseases which usually face delayed diagnostics.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A sensor device capable of performing electrochemical measurements, comprising:
    a flexible orthodontic device for placement in a patient's mouth, the flexible orthodontic device having a hole in an end configured to allow saliva to pass;
    a plurality of valves to allow the saliva to pass in a forward direction through the flexible orthodontic device and not in a reverse direction, wherein each of the plurality of valves includes a first side and a second side wider than the first side, wherein at least one of the plurality of valves is placed after another valve such that the first side of a first valve of the plurality of valves is inside the second side of a second valve of the plurality of valves arranged next to the first valve; and
    one of or more electrochemical or optical electrodes configured to contact the saliva, wherein the one or more electrochemical or optical electrodes are configured to determine a presence of one or more chemical biomarkers in the saliva.

2. The sensor device as in claim 1, further comprising:
    one or more electronic circuits to process signals from the one or more electrochemical or optical electrodes; and
    a wireless transmitter to transmit information from the processed signals to a receiving device.

3. The sensor device as in claim 1, wherein the flexible orthodontic device is part of a pacifier or a nipple.

4. The sensor device as in claim 1, wherein the one or more electrochemical or optical electrodes generate a signal representative of an amount of glucose in the saliva.

5. The sensor device as in claim 1, wherein the one or more electrochemical or optical electrodes includes at least one enzyme-based electrode selected to determine a presence of a selected biomarker of one or more chemical biomarkers in the saliva.

6. The sensor device as in claim 5, wherein the at least one enzyme-based electrode is glucose oxidase.

7. The sensor device as in claim 1, wherein the plurality of valves includes a combination of valves in a main channel causing unidirectional flow of the saliva to an electrochemical detection chamber.

8. The sensor device as in claim 7, wherein a cellulose-based thread, causes a lateral flow of the saliva from the electrochemical detection chamber to an outside of the sensor device.

9. The sensor device as in claim 1, configured to collect and dispose of the saliva without external pumps.

10. The sensor device as in claim 1, wherein the one or more electrochemical or optical electrodes are not in contact with the patient's mouth.

11. The sensor device as in claim 1, wherein the one or more electrochemical or optical electrodes are non-toxic.

12. The sensor device as in claim 1, further comprising:
    an electrochemical chamber to contain the saliva.

13. The sensor device as in claim 1, wherein the flexible orthodontic device comprises a non-toxic polymeric nipple with an inlet for collecting saliva and a safety valve system causing uni-directional saliva flow towards the one or more electrochemical or optical electrodes.

14. The sensor device as in claim 13, wherein the safety valve system includes a rectifying channel with asymmetrical conical constrictions.

15. The sensor device of claim 1, comprising:
    a cap integrated with a wireless amperometric circuit;
    an electrochemical chamber to contain the saliva for a separated electrochemical detector; and
    a safety valve system causing uni-directional saliva flow towards the electrochemical detector.

16. A method of performing electrochemical measurements, comprising:
    receiving saliva through a flexible orthodontic device comprising a nipple or pacifier with a hole in an end;
    passing the received saliva through a plurality of one or more valves allowing the saliva to pass in a forward direction and not in a reverse direction, wherein each of the plurality of valves includes a first side and a second side wider than the first side, wherein at least one of the plurality of valves is placed after another value such that the first side of a first valve of the plurality of valves is inside the second side of a second valve of the plurality of valves arranged next to the first valve; and
    contacting the saliva, by one or more electrochemical or optical electrodes, wherein the one or more electrochemical or optical electrodes are configured to determine a presence of one or more chemical biomarkers in the saliva.

17. The method as in claim 16, further comprising:
processing, by one or more electronic circuits, signals from the one or more electrochemical or optical electrodes; and
transmitting, by a wireless transmitter, information from the processed signals to a receiving device.

18. The method as in claim 16, wherein the one or more electrochemical or optical electrodes generate a signal representative of an amount of glucose in the saliva.

19. The method as in claim 16, wherein the one or more electrochemical or optical electrodes includes at least one enzyme-based electrode selected to determine a presence of a selected biomarker in the saliva.

20. An electrochemical measurement system, comprising:
an inlet module comprising a flexible orthodontic device configured to pass saliva;
a valving module including a plurality of valves and allowing the saliva to pass in a forward direction through the valving module and not in a reverse direction, wherein each of the plurality of valves includes a first side and a second side wider than the first side, wherein at least one of the plurality of valves is placed after another value such that the first side of a first valve of the plurality of valves is inside the second side of a second valve of the plurality of valves arranged next to the first valve;
a contact module including one or more electrochemical or optical electrodes configured to generate signals in response to contact with saliva; and
a processing module to process the generated signals to determine a presence of one or more chemical biomarkers in the saliva.

21. The electrochemical measurement system as in claim 20, wherein the one or more electrochemical or optical electrodes includes at least one enzyme-based electrode selected to determine a presence of a selected biomarker in the saliva.

* * * * *